(12) United States Patent
Rana et al.

(10) Patent No.: US 9,068,109 B2
(45) Date of Patent: Jun. 30, 2015

(54) NANO-ENCAPSULATED TRIGGERED-RELEASE VISCOSITY BREAKER

(71) Applicants: William Marsh Rice University, Houston, TX (US); Halliburton Energy Services, Inc., Houston, TX (US)

(72) Inventors: Rohit K. Rana, Houston, TX (US); Vinit S. Murthy, Houston, TX (US); Michael S. Wong, Houston, TX (US); Lewis R. Norman, Duncan, OK (US)

(73) Assignees: William Marsh Rice University, Houston, TX (US); Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 13/925,179

(22) Filed: Jun. 24, 2013

(65) Prior Publication Data
US 2013/0345099 A1 Dec. 26, 2013

Related U.S. Application Data

(62) Division of application No. 11/993,120, filed as application No. PCT/US2006/025026 on Jun. 26, 2006, now abandoned.

(60) Provisional application No. 60/694,039, filed on Jun. 24, 2005.

(51) Int. Cl.
*C09K 8/60* (2006.01)
*C09K 8/68* (2006.01)
(Continued)

(52) U.S. Cl.
CPC . *C09K 8/706* (2013.01); *A61K 8/11* (2013.01); *A61K 2800/412* (2013.01);
(Continued)

(58) Field of Classification Search
CPC ............. C09K 8/52; C09K 8/62; C09K 8/685
USPC ........... 507/201, 203, 239, 267, 276; 428/403
See application file for complete search history.

(56) References Cited

U.S. PATENT DOCUMENTS

| 4,506,734 A | 3/1985 | Nolte |
| 4,741,401 A | 5/1988 | Walles et al. |

(Continued)

FOREIGN PATENT DOCUMENTS

| WO | 2007002690 A2 | 1/2007 |
| WO | 2007002690 A3 | 1/2007 |

OTHER PUBLICATIONS

Bibliographic Data and specification for provisional patent application entitled "Method to encapsulate and triggered-release viscosity breakers using nanoparticle-assembled capules (NACs) as delivery agents in fracturing fluids," by Rohit K. Rana, et al., filed Jun. 24, 2005 as U.S. Appl. No. 60/694,039.

(Continued)

*Primary Examiner* — Susannah Chung
*Assistant Examiner* — Atnaf Admasu
(74) *Attorney, Agent, or Firm* — Conley Rose, P.C.; Rodney B. Carroll

(57) ABSTRACT

A method for the encapsulation and triggered-release of water-soluble or water-dispersible materials. The method comprises a) providing an amount of electrolyte having a charge, b) providing an amount of counterion having a valence of at least 2, c) combining the polyelectrolyte and the counterion in a solution such that the polyelectrolyte self-assembles to form aggregates, d) adding a compound to be encapsulated, and e) adding nanoparticles to the solution such that nanoparticles arrange themselves around the aggregates. Release of the encapsulated species is triggered by disassembly or deformation of the microcapsules though disruption of the charge interactions. This method is specifically useful for the controlled viscosity reduction of the fracturing fluids commonly utilized in the oil field.

19 Claims, 3 Drawing Sheets

(51) Int. Cl.
*C09K 8/524* (2006.01)
*C09K 8/504* (2006.01)
*B32B 27/02* (2006.01)
*C09K 8/70* (2006.01)
*A61K 8/11* (2006.01)
*A61Q 19/00* (2006.01)
*B01J 13/02* (2006.01)
*B82Y 5/00* (2011.01)
*C12N 9/96* (2006.01)
*C12N 11/04* (2006.01)

(52) U.S. Cl.
CPC .......... *A61K 2800/413* (2013.01); *A61Q 19/00* (2013.01); *B01J 13/02* (2013.01); *B82Y 5/00* (2013.01); *C09K 2208/10* (2013.01); *C12N 9/96* (2013.01); *C12N 11/04* (2013.01)

(56) References Cited

U.S. PATENT DOCUMENTS

| | | | |
|---|---|---|---|
| 4,919,209 A | 4/1990 | King | |
| 5,102,558 A | 4/1992 | McDougall et al. | |
| 5,102,559 A | 4/1992 | McDougall et al. | |
| 5,110,486 A | 5/1992 | Manalastas et al. | |
| 5,164,099 A | 11/1992 | Gupta et al. | |
| 5,204,183 A | 4/1993 | McDougall et al. | |
| 5,370,184 A | 12/1994 | McDougall et al. | |
| 5,373,901 A | 12/1994 | Norman et al. | |
| 5,437,331 A | 8/1995 | Gupta et al. | |
| 6,162,766 A * | 12/2000 | Muir et al. | 507/267 |
| 7,563,457 B2 | 7/2009 | Cha et al. | |
| 7,595,284 B2 | 9/2009 | Crews | |
| 2005/0178553 A1* | 8/2005 | Harris | 166/308.5 |
| 2010/0267594 A1 | 10/2010 | Rana et al. | |

OTHER PUBLICATIONS

Foreign communication from a related counterpart application—International Preliminary Report on Patentability, PCT/US2006/025026, Dec. 24, 2007, 7 pages.

Foreign communication from a related counterpart application—International Search Report and Written Opinion, PCT/US2006/025026, Jan. 31, 2007, 10 pages.

Office Action dated Aug. 28, 2012 (15 pages), U.S. Appl. No. 11/993,120, filed Jun. 7, 2010.

Office Action (Final) dated Mar. 28, 2013 (8 pages), U.S. Appl. No. 11/993,120, filed Jun. 7, 2010.

\* cited by examiner

NANO-ENCAPSULATED TRIGGERED-RELEASE VISCOSITY BREAKER

CROSS-REFERENCE TO RELATED APPLICATIONS

This application is a divisional of U.S. patent application Ser. No. 11/993,120, filed Jun. 7, 2010, published as US 2010/0267594 A1, now abandoned, which is a filing under 35 U.S.C. 371 of International Application No. PCT/US2006/025026 filed Jun. 26, 2006, entitled "Nano-Encapsulated Triggered-Release Viscosity Breakers," claiming priority of U.S. Provisional Patent Application No. 60/694,039 filed Jun. 24, 2005, which applications are incorporated by reference herein in their entirety, for all purposes.

FIELD OF THE INVENTION

The present invention relates to methods and compositions for controlled viscosity reduction of fracturing fluids used in subterranean formations. The method involves both encapsulation and release of viscosity breakers by using microcapsules assembled from charged nanoparticles and polyelectrolytes. During the microcapsule assembly process, breakers such as enzymes, persulphate, aminocarboxylates, etc., are encapsulated into the shell. The encapsulated species are released during the disassembly or deformation of the microcapsules induced by the addition of salt (NaCl, brine, sea water, etc.). The methods and compositions are designed in such a way that the reduction of viscosity is initiated by contacting fracturing fluids with brine solution.

This method can more generally be utilized for encapsulating water-soluble or water-dispersible materials in microcapsules assembled from nanoparticles and, as such, is useful for the encapsulation and release of a variety of materials. Such materials include, for example, fluorescent dyes, macromolecules, and enzymes. As stated above, this method is particularly useful for the encapsulation of breaker materials used to break fracturing fluids that are employed in the stimulation of subterranean formations.

BACKGROUND OF THE INVENTION

Description of the Related Art

Hydraulic fracturing of subterranean formations is done to increase permeability and flow from the formation to a well-bore. The process involves injecting a fracturing fluid into the well-bore at extremely high pressure to create fractures in the rock formation surrounding the bore. The fractures radiate outwardly from the well-bore and extend the surface area from which oil or gas drains into the well. Usually a gel, an emulsion or a foam, having a proppant such as sand or other particulate material suspended therein is introduced into the fracture. The proppant is deposited in the fracture and functions to hold the fracture open after the fluid pressure is released.

The fracturing fluid typically contains a water soluble polymer, such as guar gum or a derivative thereof, which provides appropriate flow characteristics to the fluid and suspends the proppant particles therein. When the pressure on the fracturing fluid is released, the fracture closes around the propping agent, water is forced therefrom and the water-soluble polymer forms a compact cake. This can prevent oil or gas flow if not removed. To enhance permeability, viscosity breakers may be included in the fracturing fluid and reduce the viscosity of the fracturing fluid by degrading the polymers.

Currently, breakers are typically either enzymatic breakers or oxidative breakers. Effective use of breakers requires that the onset of either enzymatic hydrolysis or oxidative breakdown of the polymer be controlled. This is needed to prevent any premature degradation of the polymer which may decrease the fluid's ability to fracture the subterranean formations.

There have been several proposed methods for the breaking of fracturing fluids aimed at eliminating the above problems. The use of capsules to mask, protect, stabilize, delay or control the release of various materials is well known and, in particular, the use of such capsules or microcapsules to encapsulate breaker materials has been described in, e.g., U.S. Pat. No. 4,741,401 to Walles et al; U.S. Pat. No. 4,919,209 to King; U.S. Pat. No. 5,110,486 to Manalastas et al; U.S. Pat. Nos. 5,102,558; 5,102,559; 5,204,183 and U.S. Pat. No. 5,370,184 all to McDougall et al; U.S. Pat. No. 5,164,099 and U.S. Pat. No. 5,437,331 to Gupta et al; and U.S. Pat. No. 5,373,901 to Norman et al.

Typically, the encapsulated breaker material is formed by surrounding the breaker material with an enclosure member that is sufficiently permeable to at least one fluid, generally water, found in a subterranean formation being treated or to a fluid injected with the capsule into the formation and which is capable of releasing the breaker. Generally the breaker is coated or encapsulated by spraying small particles of the material with a suitable coating formulation in a fluidized bed or by suspension polymerization wherein the breaker particles are suspended in a liquid-liquid system containing a monomer which is capable of polymerizing to form a polymeric coating surrounding the breaker particle.

For example, U.S. Pat. No. 4,506,734 provides a viscosity-reducing chemical contained within hollow or porous, crushable and fragile beads. When a fracturing fluid containing such beads passes or leaks off into the formation or the fluid is removed by back flowing, any resulting fractures in the subterranean formation close and crush the beads. The crushing of the beads then releases the viscosity-reducing chemical into the fluid. This process is dependent upon the pressure of the formation to obtain release of the breaker and is thus subject to varying results dependent upon the formation and its closure rate.

U.S. Pat. No. 4,741,401 discloses a method for breaking a fracturing fluid comprised of injecting into the subterranean formation a capsule comprising an enclosure member containing the breaker. The breaker is released from the capsule by pressure generated within the enclosure member due solely to the fluid penetrating into the capsule whereby the increased pressure causes the capsule to rupture, releasing the breaker. This method for release of the breaker would result in the release of the total amount of breaker contained in the capsule at one particular point in time. The patent examples disclose the use of the encapsulated breaker at temperatures ranging from room temperature, 65° C. to 85° C.

Although the foregoing methods appear to provide releasable encapsulated materials, it remains desirable to provide an alternative method and system that is more economical and gives equivalent or superior performance. In addition, there remains a need for a method that provides better control over the release of viscosity breakers, and, subsequently, sharper control of fracturing fluid viscosity.

SUMMARY OF THE INVENTION

The present invention provides a simple method for encapsulating and releasing various species using nanoparticle-assembled capsules (NACs) having spherical and non-spherical shapes. In preferred embodiments, the present methods for the encapsulation comprise providing a polyelectrolyte having a positive or negative charge, providing an oppositely charged counterion having a valence of at least 2, combining the polyelectrolyte and the counterion in a solution such that the polyelectrolyte self-assembles to form aggregates, adding the compound to be encapsulated, allowing the compound to enter the aggregates, and adding nanoparticles to the solution such that nanoparticles arrange themselves around the aggregates and encapsulate the compound.

There are numerous water-soluble or water-dispersible compounds that may be encapsulated, including enzymes, organic dyes, sols such as a ferro fluids, magnetic contrast agents, and cosmetics. The method may be carried out at ambient temperature.

In some embodiments, the final step produces sub-micron or micron-sized organic-inorganic spheres in which the shell consists of nanoparticles and polyelectrolyte molecules that hold the nanoparticles together. The method may further include functionalizing the polyelectrolyte with at least one moiety selected from the group consisting of: organic molecules, organic fluorophores, and biomolecules. Alternatively, or in addition, the nanoparticles may be functionalized. A variety of organic and inorganic nanoparticles such as metals, metal oxides, metal-non-oxides, organic particles, linear polymers, biomolecules, fullerenols, and single/multi-walled carbon nanotubes can be used.

The herein presented method to encapsulate and release breakers and various other species using hybrid microcapsules offers several advantages. The method is extremely simple to carry out, allows huge flexibility in materials composition, and can be made environmentally and economically favorable. The ease of encapsulating a wide variety of compounds makes it viable for a broad spectrum of applications. The one-step method of encapsulation during the assembly of NACs occurs in one pot, and thus there is no need for a large synthesis set-up. NACs can be used to encapsulate both enzymatic and oxidative viscosity breakers. The one-step method of releasing the encapsulate by salt-induced disruption of NACs is simple and does not require any harsh conditions, as opposed to the extreme pH and/or temperature treatments generally employed in other methods. These mild synthesis conditions, which cover a wide pH range, allow the encapsulation of sensitive organic compounds that would otherwise be degraded. And, finally, the present composition and processes can easily be adapted to the procedures for using breaker-containing fracturing fluids currently employed in the stimulation of subterranean formations.

Thus, the present invention comprises a combination of features and advantages that enable it to overcome various problems of prior methods. The various characteristics described above, as well as other features, will be readily apparent to those skilled in the art upon reading the following detailed description of the preferred embodiments of the invention, and by referring to the accompanying drawings.

BRIEF DESCRIPTION OF THE DRAWINGS

For a more detailed description of the preferred embodiment of the present invention, reference will now be made to the accompanying drawings, wherein.

DETAILED DESCRIPTION OF THE PREFERRED EMBODIMENT

The present approach involves nanoparticle assembled microcapsules (NACs) designed to carry and deliver breakers. The process herein presented, of polymer self-association in water followed by nanoparticle deposition and creation of (sub)micron-sized colloidal microcapsule structures, can be used to encapsulate water-soluble compounds. Specifically, cationic polyamines form supramolecular spherical aggregates in the presence of multivalent anions through ionic crosslinking, and negatively-charged 12-nm silica nanoparticles electrostatically deposit around the aggregates to form a closed shell. In order to encapsulate water soluble compounds such as enzyme or dye molecules inside these microcapsules, the chosen compounds are added to the polymer aggregates prior to the addition of silica nanoparticles. By electrostatic interaction, the encapsulating compounds penetrate into the aggregates. Upon addition of silica nanoparticles, the enclosing shell formation takes place, encapsulating the desired compounds within. Compounds that can be encapsulated include but are not limited to enzymatic breakers such as β-Mannanase.

Since the shells of the present microcapsules are made up of nanoparticles and polymer chains held together by electrostatic interaction, the structure can be disassembled or deformed by changing the ionic strength of the aqueous suspension. The addition of a proper amount of NaCl or brine solution, for example, effects the release of the encapsulated materials from the microcapsules. The deformation of the microcapsules was verified using confocal and optical microscopy. The salt-induced release of the encapsulated materials from the microcapsules provides a convenient way to control the release profile, which may lead to wider applications such as oil-field applications, drug delivery, etc.

Figure 1:
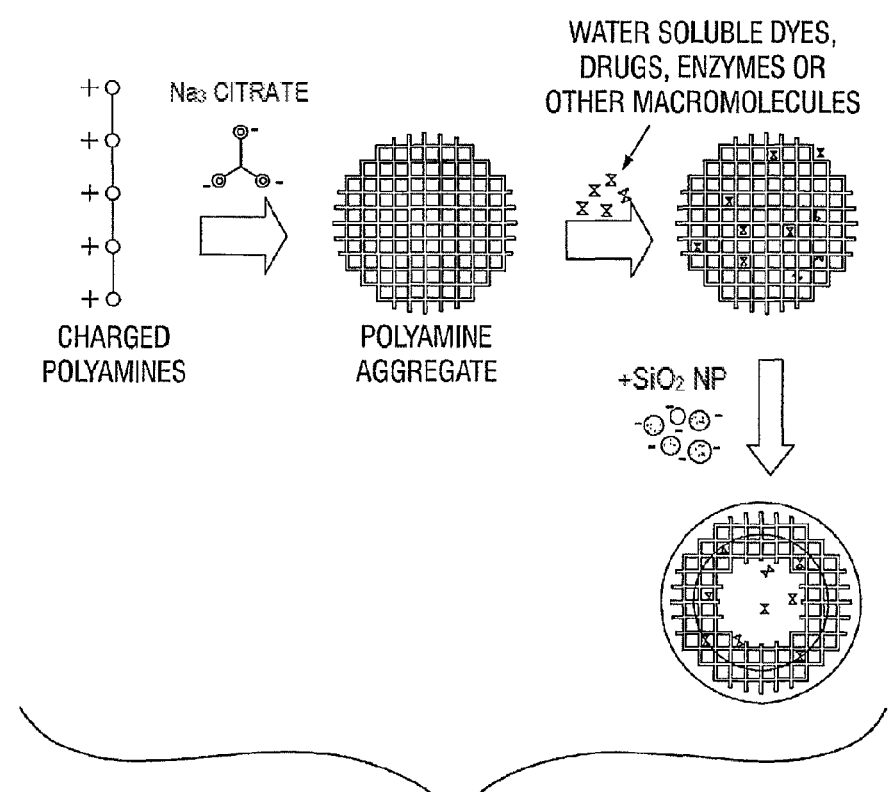
FIG. 1 is a schematic representation of the encapsulation process.

Polyamines have been used as the structure-directing agent in the presence of multivalent anions (e.g., sodium sulfate, trisodium citrate). The general steps for carrying out one embodiment of the method for the encapsulation of breakers are discussed in detail below and are shown in FIG. 1.

Briefly, a desired concentration of polyamines is dissolved in water. A solution of a desired salt of a multivalent anion is added to the polyamine solution, at which point the counterions mediate the self-assembly of polyamines to form spherical salt-bridged polyamine aggregates. The compound (enzyme or other species) of interest (to be encapsulated) is then added to the polymer-counterion aggregates. The suspension is aged for a certain period, during which time the enzyme or other species penetrates the aggregates. Next, a sol of a preselected type of nanoparticle is added to the same suspension, whereupon these nanoparticles arrange themselves around the polymer aggregates, thus encapsulating the enzyme or other desired molecules. The resulting product is sub-micron/micron-sized organic-inorganic spheres, in which the thick shell consists of nanoparticles and the polyamine molecules.

The suspension of enzyme-containing NACs can be used as-is or separated from the mother-liquor by centrifugation for their further use. For example, it may be desirable to separate the NACs for use in viscosity reduction in a fracturing fluid. By way of example only, enzyme-containing NACs may be added to a guar gel either at room temperature or elevated temperatures. When desired, a sufficient amount of salt (NaCl or brine) can be added to the mixture of guar gel and enzyme-containing NACs so as to cause the release of enzyme from the NACs.

To encapsulate the breaker persulfate, its corresponding salt can be used as the anionic species to crosslink the polymer, forming spherical aggregates.

For the embodiment presented in FIG. 1, the encapsulated compound is preferably negatively charged in order to ensure effective encapsulation into the polyamine aggregates due to electrostatic interaction with the positive charges on the polymer. The charge on the encapsulated compound can be controlled by changing the pH of the solution.

Examples

According to preferred embodiments, one method for preparing nanoparticle assembled microcapsules (NACs) involves poly-L-lysine (PLL) as the polyamine, citrate (cit) as the multivalent anion and silica nanoparticles. β-Mannanase (Megazyme) is used as the enzymatic breaker. For the enzyme encapsulation in NACs, 25 μL of the enzyme solution (9 U/ml β-Mannanase) was mixed with 21 μL of PLL and aged for 25 minutes. The resulting solution was added to a previously aged (25 min) PLL/cit suspension. The suspension was then aged for another 5 minutes. To this, a colloidal sol of silica nanoparticles was added and formed a thick shell surrounding the aggregates.

Optical brightfield and confocal images of silica microcapsules encapsulating β-Mannanase enzyme show circular microcapsules. The composition comprises: 21 μL PLL-FITC (2 mg/ml, 68.6 kD)+125 μL $Na_3Cit$ (5.36 mM)+50 μL β-Mannanase enzyme (9 units/ml)+125 μL $SiO_2$ NP (20 wt %).

The encapsulation of the enzyme within the resultant NACs was verified by checking its activity in a 0.5 wt % guar solution. The guar solution was prepared by sprinkling 0.25 g of Guar to 49.75 g of DI water. After mixing, the solution was further stirred for 5 minutes and then aged for another 10 minutes without stirring. The enzyme-containing NAC suspension was then added to the guar solution while stirring. Viscosity was measured after specific times using a fann Viscometer (Model 35A). Bob deflection values were obtained at 100, 200, 300 and 600 rpm, which correspond to 170, 340, 511 and 1021 l/sec shear rates, respectively. Viscosity was calculated from the deflection values using instrument conversion factors.

Figure 2:
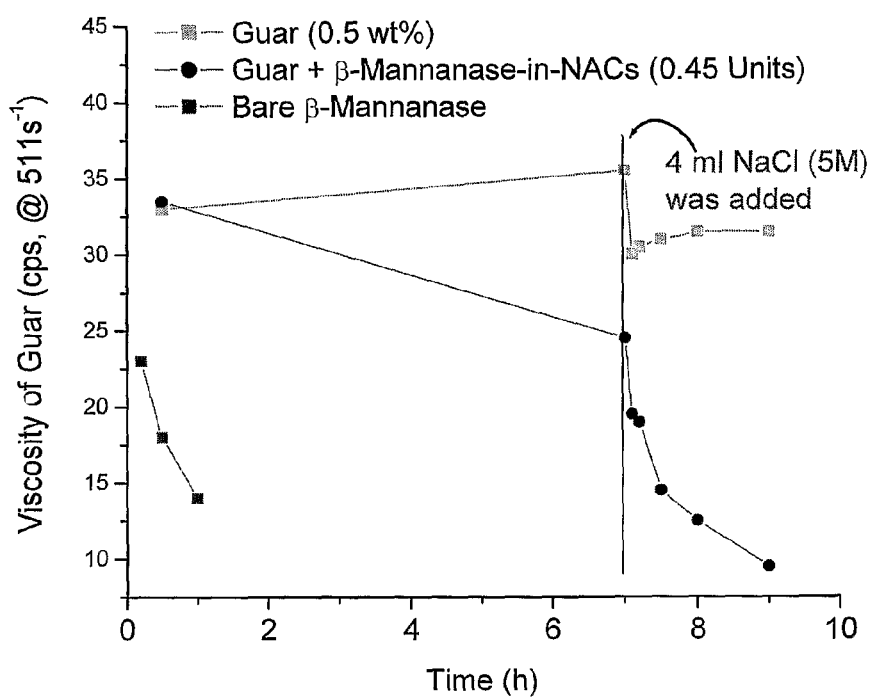
FIG. 2 is a graph showing the viscosity of guar gel with time at room temperature.

The stability of enzyme-containing NACs and triggered-release of the enzyme from NACs at room temperature are shown in FIG. 2. The graph shows the change in viscosity of 0.5 wt % guar gel (with or without containing β-Mannanase enzyme (0.45 Units) encapsulated in NACs) with time. After 7 hours, 4 ml of 5M NaCl was added to the gel. [Composition: 21 μL PLL-FITC (2 mg/ml, 68.6 kD)+125 μL $Na_3Cit$ (5.36 mM)+50 μL β-Mannanase enzyme (9 units/ml)+125 μL $SiO_2$ NP (20 wt %)].

Figure 3:
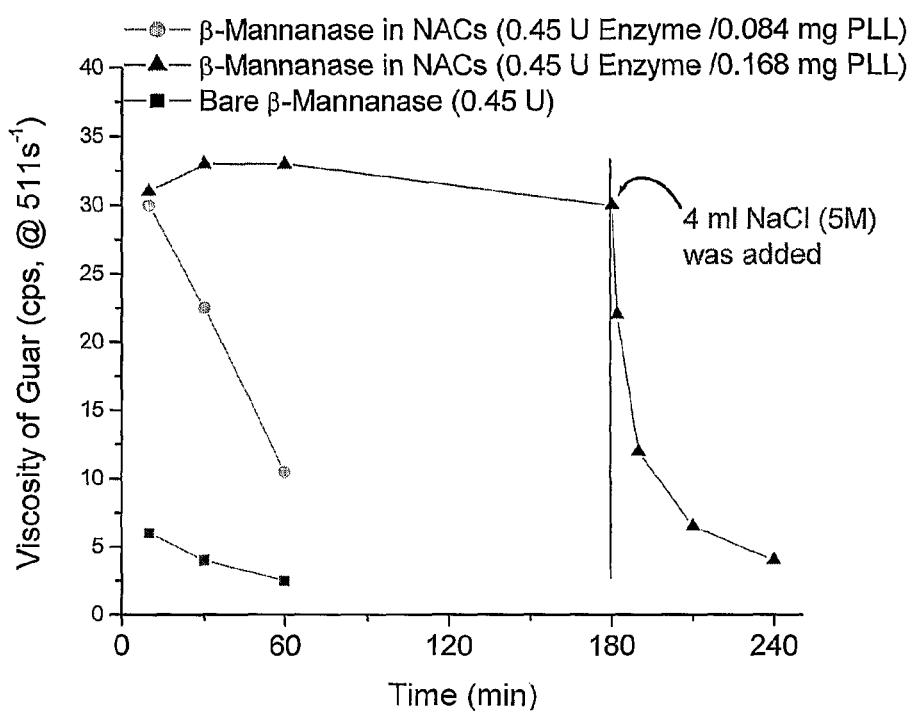
FIG. 3 is a graph showing the viscosity of guar gel with time at 50° C.

As FIG. 2, FIG. 3 presents the stability of enzyme-containing NACs and triggered-release of the enzyme from NACs at a temperature of 50° C. The graph shows the change in viscosity of 0.5 wt % guar gel containing the bare or encapsulated enzyme (0.45 Units) in NACs with time at 50° C. After 3 hours, 4 ml of 5M NaCl was added to the gel. [Compositions: (circles) two batches of (21 μL PLL-FITC (2 mg/ml, 68.6 kD)+125 μL $Na_3Cit$ (5.36 mM)+25 or 50 μL β-Mannanase enzyme (9 units/ml)+125 μL $SiO_2$ NP (20 wt %)); (triangles) two batches of (42 μL PLL-FITC (2 mg/ml, 68.6 kD)+125 μL $Na_3Cit$ (5.36 mM)+25 μL β-Mannanase enzyme (9 units/ml)+125 μL $SiO_2$ NP (20 wt %)].

The present process can be used to encapsulate and release enzymatic breakers, and oxidizing and chelating agents, thus having potential usage in oil field applications. The method to assemble and disassemble these microcapsules also provides opportunities for applications in areas as diverse as drug delivery, chemical storage, contaminated waste removal, gene therapy, catalysis, cosmetics, magnetic contrast agents (for use in magnetic resonance imaging), and magneto-opto-electronics. It should be emphasized that for many of the above applications the method provides flexibility to meet the required reaction conditions such as pH of the medium, temperature, etc., for specific applications.

The present methods are extremely amenable to variations, as discussed below.

Encapsulation of Breakers in NACs

As described herein, NACs can be assembled from negatively charged polymers and positively charged nanoparticles. Charged polymers having additional functional groups that will provide sites for the breakers to anchor and thereby encapsulate into the NACs can also be employed. The method can involve cationic counterions such as metal ions (e.g., $Ca^{2+}$) that can have applications in controlling the rate of cement binding in oil-field operations.

Ethylenediamine tetraacetate, EDTA, can serve as the anionic counteranion, and can also act as a viscosity breaker in the fracturing fluid. Moreover, the polymers may be functionalized with organic molecules, organic fluorophores, or biomolecules before the formation of the encapsulating nanoparticle shell, or the nanoparticles themselves may be functionalized to have active species on the outer surface of the spheres. Salt granules (salts of persulfate, perchlorate, $Ca^{2+}$ etc.) can be utilized for encapsulation, and the encapsulation can be performed by assembling charged polymers and then silica nanoparticles on the surface of these granules.

Modification of the NACs

After formation, the surface of the NACs can be treated with organic molecules for targeting the delivery site, or with nanoparticles for compositional and structural variations.

Alternate Methods for Disassembly or Deformation of the NACs

The NACs can be disassembled or deformed by various methods, including, but not limited to, changing the ionic strength upon addition of solutions other than NaCl such as brine or sea water, changing the pH of the aqueous suspension, and osmotic pressure.

Modifications of the Method to Encapsulate and Deliver Using NACs

The method as herein described can be performed at different pH conditions and/or synthesis temperatures, using different solvents, and the synthesis of the microcapsules containing breakers could be carried out in a flow-type reactor, such as microfluidic device and aerosol reactor.

Use of NACs Assembled from NPs Other than Silica

Charged NPs include: metal nanoparticles, such as gold, platinum, palladium, copper, silver, rhodium, rhenium, nickel, and iridium having surface positive/negative charge, alloys of metal nanoparticles, such as platinum/iridium having surface positive/negative charge, metal non-oxide nanoparticles, such as II-VI, III-V, and IV quantum dots having surface positive/negative charge, metal oxide nanoparticles, such as titanium oxide, zirconium oxide, aluminum oxide, iron oxide, tungsten oxide, cerium oxide, antimony oxide and silicon oxide having surface positive/negative charge, and nanoparticles functionalized with cationic/anionic polymers that can be assembled by adding suitable counterions. Nanoparticles may also be functionalized with molecules to provide a hydrophilic or hydrophobic surface. The use of hydrophobic nanoparticles, such as polystyrene and polypyrrole may be envisioned. Furthermore, nanoparticles may have diameters of 1-100 nm and may have shapes other than spheres, such as rods, triangles, and hexagons. Additionally, combinations of nanoparticles may be employed.

Use of NACs Assembled from Cationic Polymer, Anionic Counterions and Negatively Charged NPs Cationic polymers and anionic counterions that can be used in the present invention include but are not limited to: polypeptides and polyamines with different chain lengths with straight or branched structure, anionic counterions with different functional groups, such as carboxylates, phosphates and sulfates (e.g. phosphate and sulfate analogs of citrate and EDTA), and counterions such as peptides, polypeptides, copolypeptides and polymers having negative charge (e.g. aspartic acid and glutamic acid).

Use of NACs Assembled from Anionic Polymer, Cationic Counterions and Positively Charged Nanoparticles Likewise, suitable anionic polymers and cationic counterions include: polypeptides and polyacids with different chain lengths with straight or branched structure, cationic counterions such as metal ions ($Ca^{2+}$, $Mg^{2+}$, transition metal ions, etc.), and counterions such as peptides, polypeptides, copolypeptides and polymers having positive charge (e.g. lysine and histidine).

Alternate Polymers

Other polymers can be utilized, including cationic/anionic polymers functionalized with organic molecules, biomolecules and fluorophores, the blocks of the copolypeptides derived from the 20 natural amino acids (lysine, arginine, histidine, aspartic acid, glutamic acid, glycine, alanine, valine, leucine, isoleucine, methionine, proline, phenylalanine, tryptophan, serine, threonine, asparagine, glutamine, tyrosine, and cysteine), and combinations of polypeptides.

Applications in Other Areas

The herein disclosed method may find application in other areas, such as the encapsulation of enzymes for biochemical reactions, the encapsulation of organic dyes, the encapsulation of a sol within the interior of the hollow spheres, such as a ferro-fluid, as well as applications in drug delivery, chemical storage, contaminated waste removal, gene therapy, catalysis, cosmetics, magnetic contrast agents (for use in magnetic resonance imaging), and magneto-opto-electronics.

While preferred embodiments of this invention have been shown and described, modifications thereof can be made by one skilled in the art without departing from the scope of this invention. The embodiments described herein are exemplary only and are not limiting. Accordingly, the scope of protection is not limited to the embodiments described herein, but is only limited by the claims which follow, the scope of which shall include all equivalents of the subject matter of the claims. In the claims that follow, any sequential recitation of steps is not intended as a requirement that the steps be performed sequentially, or that one step be completed before another step is begun, unless explicitly so stated. The disclosures of all patents, patent applications and publications cited herein are hereby incorporated herein by reference to the extent that they describe materials, methods or other details supplementary to those set forth herein.

What is claimed is:

1. A method of servicing a wellbore in a subterranean formation comprising:
   (a) preparing a wellbore servicing a fluid comprising a nanoencapsulate containing a wellbore servicing additive, wherein the nanoencapsulate is prepared by:
      i) providing an amount of a polyelectrolyte having a charge;
      ii) providing an amount of a counterion having a valence of at least 2;
      iii) combining the polyelectrolyte and the counterion in a solution such that the polyelectrolyte self-assembles to form aggregates;
      iv) adding to the aggregates the wellbore servicing additive to be encapsulated; and
      v) adding nanoparticles to the solution such that the nanoparticles arrange themselves around the aggregates to form nanoencapsulates that encapsulate the wellbore servicing additive; and
   (b) introducing the wellbore servicing fluid to the wellbore, wherein the wellbore servicing additive is released from the nanoencapsulates into the wellbore and/or surrounding formation and wherein the release of the wellbore servicing additive occurs following the addition of a salt solution to the wellbore servicing fluid in an amount effective to produce deformation of the nanoencapsulates.

2. The method of claim 1 wherein the wellbore servicing additive comprises a breaker, an oxidizing agent, or a chelating agent.

3. The method of claim 2 wherein the breaker comprises an enzymatic breaker, a viscosity breaker or combinations thereof.

4. The method of claim 3 wherein the enzymatic breaker comprises β-Mannanase.

5. The method of claim 1 wherein the polyelectrolyte comprises a cationic polymer and the counterion comprises a multivalent anion.

6. The method of claim 5 wherein the cationic polymer comprises a polypeptide, a polyamine, or combinations thereof.

7. The method of claim 5 wherein the multivalent anion comprises trisodium citrate, ethylenediamine tetraacetate, phosphates, carboxylates, negatively charged polymers, sulfates, or combinations thereof.

8. The method of claim 1 wherein the polyelectrolyte comprises an anionic polymer and the counterion comprises a multivalent cation.

9. The method of claim 1 wherein the nanoencapsulate comprises (sub)-micron-sized colloidal microcapsule structures.

10. The method of claim 1 wherein the nanoencapsulate comprises a polymer aggregate core and an enclosing shell comprising nanoparticles.

11. The method of claim 1 wherein the wellbore servicing additive is released from the nanoencapsulates via subjecting the nanocapsulates to changes in ionic strength, changes in pH, changes in temperature, changes in pressure or combinations thereof.

12. The method of claim 1 wherein the wellbore servicing fluid is a fracturing fluid.

13. The method of claim 1 wherein the nanoparticles comprise metals, organic particles, linear polymers, biomolecules, fullerenols, single walled carbon nanotubes, multi-walled carbon nanotubes, or combinations thereof.

14. The method of claim 10 wherein the nanoparticles are functionalized.

15. The method of claim 10 wherein the nanoparticles comprises silica.

16. A method of servicing a wellbore in a subterranean formation comprising:

(a) preparing a fracturing fluid comprising a nanoencapsulate containing a wellbore servicing additive wherein the nanoencapsulate is prepared by
   (i) providing an amount of a polyelectrolyte having a charge;
   (ii) providing an amount of a counterion having a valence of at least 2;
   (iii) combining the polyelectrolyte and the counterion in a solution such that the polyelectrolyte self-assembles to form aggregates;
   (iv) adding to the aggregates the wellbore servicing additive; and
   (v) adding nanoparticles to the solution such that the nanoparticles arrange themselves around the aggregates to form nanoencapsulates; and
(b) placing the fracturing fluid into the subterranean formation via the wellbore wherein the wellbore servicing additive is released from the nanoencapsulate and wherein the release of the wellbore servicing additive occurs following the addition of a salt solution to the wellbore servicing fluid in an amount effective to produce deformation of the nanoencapsulates.

17. The method of claim 16 wherein the nanoparticles comprise silica.

18. The method of claim 16 wherein the wellbore servicing additive comprises an enzymatic breaker, a viscosity breaker or combinations thereof.

19. The method of claim 5 wherein the multivalent anion comprises sodium sulfate.

\* \* \* \* \*